(12) United States Patent
Hotter

(10) Patent No.: US 10,130,365 B2
(45) Date of Patent: *Nov. 20, 2018

(54) WOUND CLOSURE DEVICE

(71) Applicant: Covidien LP, Mansfield, MA (US)

(72) Inventor: Joseph Hotter, Delmar, NY (US)

(73) Assignee: Covidien LP, Mansfield, MA (US)

( * ) Notice: Subject to any disclaimer, the term of this patent is extended or adjusted under 35 U.S.C. 154(b) by 121 days.

This patent is subject to a terminal disclaimer.

(21) Appl. No.: 15/165,184

(22) Filed: May 26, 2016

(65) Prior Publication Data

US 2016/0262753 A1  Sep. 15, 2016

Related U.S. Application Data

(63) Continuation of application No. 13/211,396, filed on Aug. 17, 2011, now Pat. No. 9,375,208.

(60) Provisional application No. 61/428,301, filed on Dec. 30, 2010.

(51) Int. Cl.
*A61B 17/08* (2006.01)
*A61B 17/00* (2006.01)
*A61B 17/064* (2006.01)

(52) U.S. Cl.
CPC .......... *A61B 17/08* (2013.01); *A61B 17/0057* (2013.01); *A61B 17/0644* (2013.01); *A61B 2017/00654* (2013.01); *A61B 2017/00668* (2013.01); *A61B 2017/00867* (2013.01); *A61B 2017/00871* (2013.01); *A61B 2017/0641* (2013.01); *A61B 2017/081* (2013.01)

(58) Field of Classification Search
CPC .......... A61B 17/0057; A61B 2017/081; A61B 2017/0641; A61B 2017/00654
See application file for complete search history.

(56) References Cited

U.S. PATENT DOCUMENTS

| | | | |
|---|---|---|---|
| 6,663,633 B1 * | 12/2003 | Pierson, III | A61B 17/0469 606/148 |
| 7,255,801 B2 | 8/2007 | Chen | |
| 7,811,295 B2 | 10/2010 | Kortenbach | |
| 9,375,208 B2 | 6/2016 | Hotter | |
| 2002/0077661 A1 | 6/2002 | Saadat | |

(Continued)

FOREIGN PATENT DOCUMENTS

| WO | 9826719 A1 | 6/1998 |
|---|---|---|
| WO | 9913779 A2 | 3/1999 |

(Continued)

OTHER PUBLICATIONS

European Search Report for corresponding EP11195988 dated Apr. 4, 2012 (7 pgs).

(Continued)

*Primary Examiner* — Alexander Orkin

(57) ABSTRACT

A wound closure device for positioning within a wound gap defined between at least two tissue segments has an effect of drawing the at least two tissue segments to a state of proximity that closes the wound gap. The wound closure device includes a tubular collapsible member having an expanded configuration and a collapsed configuration. The wound closure device further includes tissue engaging structure for attaching the tissue segments to the tubular collapsible member.

16 Claims, 10 Drawing Sheets

(56) References Cited

U.S. PATENT DOCUMENTS

| | | | |
|---|---|---|---|
| 2003/0093117 A1* | 5/2003 | Saadat | A61B 5/4238 |
| | | | 606/221 |
| 2003/0225420 A1 | 12/2003 | Wardle | |
| 2005/0010248 A1 | 1/2005 | Lafontaine | |
| 2005/0131460 A1 | 6/2005 | Gifford et al. | |
| 2005/0234508 A1 | 10/2005 | Cummins et al. | |
| 2006/0034930 A1* | 2/2006 | Khosravi | A61B 17/00491 |
| | | | 424/484 |
| 2007/0203511 A1* | 8/2007 | Vardi | A61B 17/00234 |
| | | | 606/153 |
| 2008/0051830 A1* | 2/2008 | Eidenschink | A61B 17/0057 |
| | | | 606/213 |
| 2008/0125860 A1 | 5/2008 | Webler et al. | |
| 2008/0135054 A1 | 6/2008 | Callister et al. | |
| 2008/0300628 A1 | 12/2008 | Ellingwood | |
| 2010/0049246 A1 | 2/2010 | Obermiller et al. | |
| 2010/0191279 A1 | 7/2010 | Kassab et al. | |
| 2012/0016411 A1 | 1/2012 | Tuval | |

FOREIGN PATENT DOCUMENTS

| | | |
|---|---|---|
| WO | 2004087235 A2 | 10/2004 |
| WO | 2012009505 A1 | 1/2012 |

OTHER PUBLICATIONS

European Office Action dated Dec. 8, 2016, issued in EP Application No. 11 195 988.

\* cited by examiner

WOUND CLOSURE DEVICE

CROSS-REFERENCE TO RELATED APPLICATIONS

This application is a Continuation of U.S. patent application Ser. No. 13/211,396 filed Aug. 17, 2011, which claims benefit of and priority to U.S. Provisional Application No. 61/428,301 filed Dec. 30, 2010, and the disclosures of each of the above-identified applications are hereby incorporated by reference in their entirety.

BACKGROUND

Technical Field

The present disclosure relates generally to surgical fasteners and particularly relates to a wound closure device to be inserted into a wound gap between tissue segments to close the wound gap by approximating the tissue segments.

Description of Related Art

A puncture wound is caused by an object piercing skin and subcutaneous tissue, and creating a hole therein. A surgical wound is an incision through skin and subcutaneous tissue made during surgery. In order to minimize scarring, prevent infection and speed recovery time, wound closure devices are typically used at the wound site to close the wound gap. Typical wound closure devices include sutures, staples and adhesive tapes. Each of the above devices has its own drawback. More specifically, suturing is a time consuming process and requires great dexterity to properly close the wound. With respect to the use of a staple as a wound closure device, it may be difficult to apply staples to the internal surfaces of a wound, such as a deep puncture wound. For a similar reason, it also may be difficult to apply an adhesive tape to the internal surfaces of a wound.

Thus, there is a need for a wound closure device that provides a simple and fast approach for deployment in a wound, such as a deep puncture wound, to accelerate rehabilitation and provide optimal efficiency in closing the wound internally and externally.

SUMMARY

Disclosed herein is a wound closure device for closing a wound gap defined by at least two tissue segments. The wound closure device of the present invention comprises a tubular collapsible member defining a proximal end, a distal end, a longitudinal axis and a hollow bore extending along the longitudinal axis between the proximal and distal ends. The wound closure device further comprises a tissue engaging structure supported on an outer wall of the tubular collapsible member positioned to engage the at least two tissue segments. The tubular collapsible member defines a first configuration in which the hollow bore is open. Additionally, the tubular collapsible member defines a second configuration in which the hollow bore is substantially closed. Further, the tubular collapsible member is selectively movable from the first configuration to the second configuration to draw the at least two tissue segments towards each other such that the wound gap is substantially closed.

In one embodiment, the tubular collapsible member is fabricated from a shape memory material that enables the member to possess a temporary shape and a permanent shape. Specifically, the first configuration of the member corresponds to the temporary shape, whereas the second configuration of the member corresponds to the permanent shape.

In a certain embodiment, the tissue engaging structure comprises a plurality of barbs configured to penetrate the at least two tissue segments. The plurality of barbs define a first angle with respect to the longitudinal axis of the tubular collapsible member before contacting the at least two tissue segments, and define a second angle with respect to the longitudinal axis upon contacting the as least two tissue segments when the tubular collapsible member enters the wound gap in an insertion direction. The plurality of barbs resume the first angle with respect to the longitudinal axis upon an application of force in a direction opposite to the insertion direction.

In another embodiment, the tubular collapsible member is operatively connected to a vacuum such that the vacuum facilitates transiting the tubular collapsible member from the first configuration to the second configuration.

In an alternate embodiment, the wound closure device comprises a suture disposed in the tubular collapsible member. An application of force on the suture effects movement of the tubular collapsible member from the first configuration to the second configuration.

DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
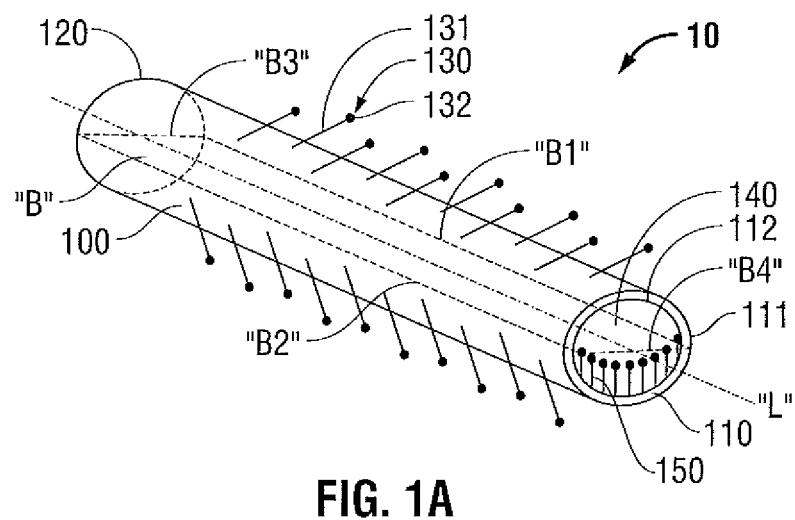
FIG. 1A is an isometric perspective view of a wound closure device in accordance with the principles of the present disclosure illustrating a tubular collapsible member in a first, expanded configuration.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. As used herein, "penetrate" refers to entering a layer of the skin without necessarily passing completely therethrough, whereas "pierce" refers to entering a layer of the skin by completely passing therethrough. In the following description, well-known functions or constructions are not described in detail to avoid obscuring the present disclosure in unnecessary detail.

The presently disclosed device described herein may be used to close a puncture wound, a surgical wound or other types of wounds that may require simple and efficient closure.

Figure 1B:
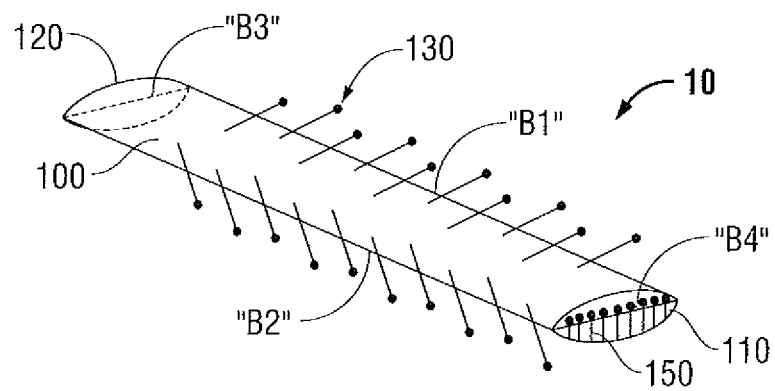
FIG. 1B is an isometric perspective view of the wound closure device of FIG. 1A in a second, collapsed configuration.

Referring now to the drawings, in which like reference numerals identify identical or substantially similar parts throughout the several views, FIGS. 1A-1B illustrate a wound closure device 10 comprising a tubular collapsible member 100 in accordance with the principles of the present disclosure. The tubular collapsible member 100 is adapted for insertion within a wound gap defined between at least two tissue segments and will be described in greater detail below.

With reference to FIGS. 1A-1B, the tubular collapsible member 100 defines a longitudinal axis "L", and includes a proximal end 110, a distal end 120, an outer wall 111 and an inner wall 112. The inner wall 112 of the member 100 defines a hollow bore 140 extending along the longitudinal axis "L" between the two ends 110 and 120. The tubular collapsible member 100 includes a tissue engaging structure 130 extending radially outwardly from the outer wall 111. In one embodiment, the tissue engaging structure 130 extends outwardly in a proximal direction from the outer wall 111 of the tubular collapsible member 100. The tissue engaging structure 130 is configured to penetrate tissue segments at the wound site to safely anchor the tubular collapsible member 100 at the wound site and securely attach the tissue segments to the outer wall 111 of the tubular collapsible member 100. The tissue engaging structure 130 may be in the form of a plurality of barbs 130, which are selectively positioned along the length of the member 100 between the proximal end 110 and the distal end 120. Additionally, the plurality of barbs 130 may be placed to circumferentially surround the outer wall 111 of the member 100, and may be configured to have a uniform length or various lengths.

Figure 1C:
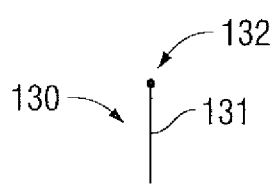
FIG. 1C is a side view of a barb associated with the wound closure device of FIG. 1A.

In one embodiment, as seen in FIG. 1C, each barb 130 comprises a slender, lengthy body 131 with a first end rooted in the outer wall 111 of the tubular collapsible member 100, and a second end with a head 132 mounted thereto. As shown in FIG. 1A, the second end locates not only radially outwardly with respect to the first end, but also locates more proximally as compared to the first end. The head 132 defines a radial diameter substantially greater than that of the body 131. The slender profile of the body 131 reduces friction encountered by the barb 130 during its penetration into the tissue segment thereby expediting the penetration process. Further, the slender profile of the body 131 reduces stress experienced by the tissue segment thereby reducing any pain that might be experienced by the patient. The relatively larger radial profile of the head 132 permits the head 132 to hook or grasp surrounding tissue to prevent the tissue from slipping off the head 132 with an effect of securely attaching the tissue to the tubular collapsible member 100. Alternately, other barb configurations are envisioned.

Referring again to FIG. 1A, in one embodiment, a plurality of barbs 150 are positioned at the proximal end 110 of the member 100. Each barb 150 also has a body and a head as described with respect to the barbs 130. Alternately, other barb configurations are envisioned. The barbs 150 stem from the inner wall 112 of the member 100 and extend radially inwardly towards the center of the hollow bore 140. As shown in FIG. 1A, the barbs 150 are all placed along one side of the inner wall 112 and are configured to grip or engage the opposing side of the inner wall 112 when the two sides of the inner wall 120 meet. Alternately, barbs 150 may be positioned along the longitudinal length of the inner wall 112, along any portion of the length, or at selected locations along the length of the inner wall 112. In another alternate embodiment, barbs 150 may be replaced with other means for securing opposing surfaces of the inner wall 112 together, e.g., adhesive.

The tubular collapsible member 100 defines a first configuration in which the member 100 is in a fully expanded state and has a maximum profile as seen in FIG. 1A. In the first configuration, the hollow bore 140 defines a maximum diameter, achieving a maximally expanded state. In addition, the tubular collapsible member 100 defines a second configuration in which the member 100 is in a substantially deflated or collapsed state and has a minimum profile as illustrated in FIG. 1B. In the second configuration, the inner wall 112 of the member 100 collapses against itself, and substantially or entirely diminishes the hollow bore 140. Also, in the second configuration, as the inner wall 112 is collapsed to the second configuration, the barbs 150 securely engage the opposite side of the inner wall 112 to retain the member 100 in the collapsed state.

Figure 2A:
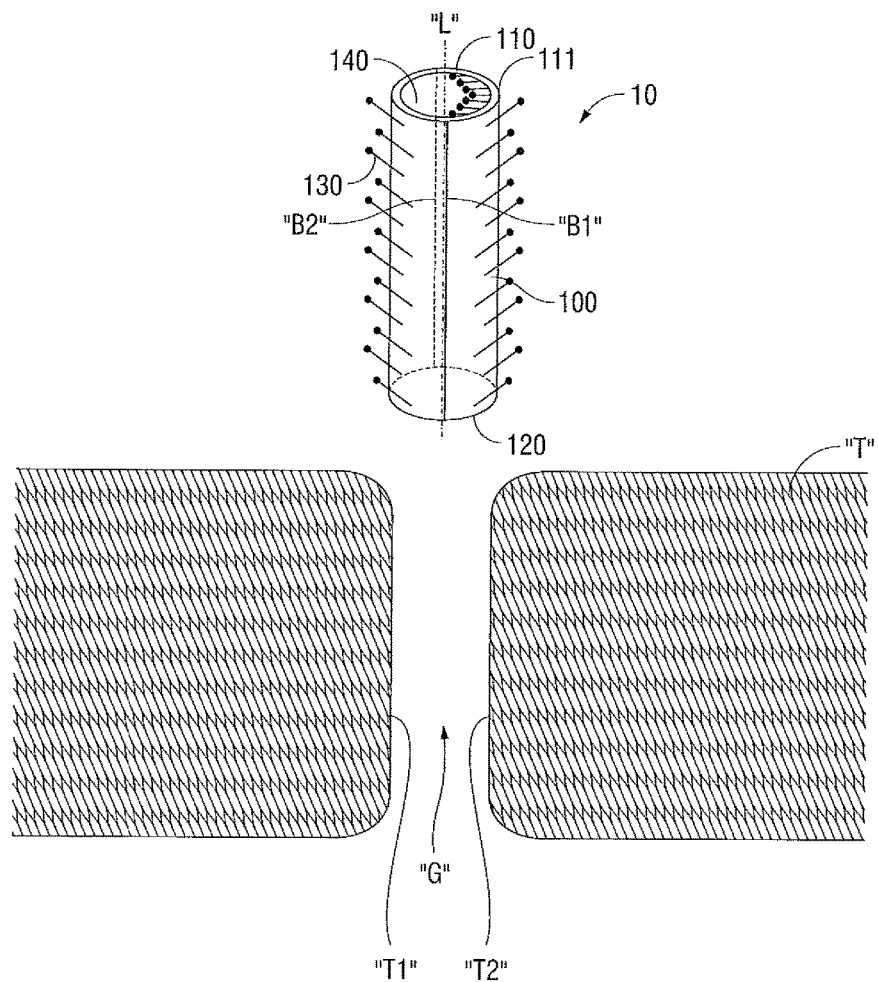
FIG. 2A is a front perspective view of the wound closure device of FIG. 1A placed above a wound gap.
Figure 2B:
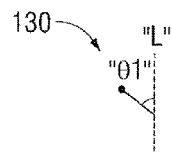
FIG. 2B is a schematic view of the barb of the wound closure device of FIG. 2A illustrating its orientation relative to a longitudinal axis of the device.

The application of the wound closure device 10 to a wound site is explained with reference to FIGS. 2A-6. With reference to FIG. 2A, the wound site comprises a wound gap "G" formed between tissue segments "T1" and "T2." The wound closure device 10 in its first, fully expanded configuration is placed directly above the wound gap "G" before its deployment therein. Before contacting the tissue segments, the barbs 130 are in an unstressed or unbiased condition, i.e., a straightened position. In the straightened position, all barbs 130 project outwardly and proximally from the outer wall 111 of the member 100. More specifically, in the straightened position, as illustrated in FIG. 2B, each barb 130 forms an acute angle "θ1" with respect to the longitudinal axis "L". Due to the proximal orientation of the barbs 130, the barbs 130 minimize potential friction that may be otherwise encountered during the insertion process of the member 100 thereby making the member 100 compilable for distal insertion into the gap "G".

Figure 3A:
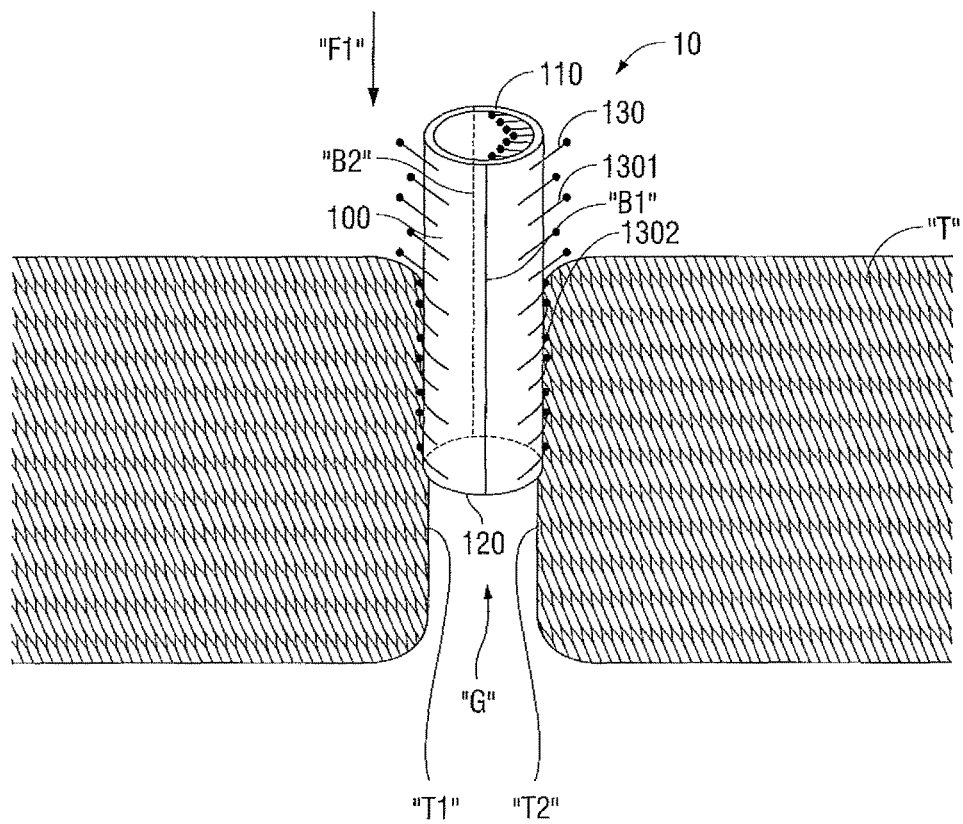
FIG. 3A is a front perspective view of the wound closure device of FIG. 1A as it is inserted into the wound gap.
Figure 3B:
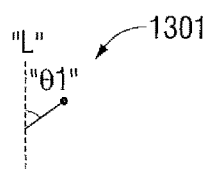
FIG. 3B is a schematic view of a barb of the wound closure device of FIG. 3A in a straightened position.
Figure 3C:
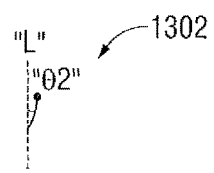
FIG. 3C is a schematic view of a barb of the wound closure device of FIG. 3A in a flexed position.

With reference to FIG. 3A, to insert the device 10 into the wound gap "G", the distal end 120 of the member 100 is positioned adjacent to an opening of the wound gap "G", and a distal force "F1" is applied to the member 100. As the member 100 moves into the gap "G", barbs 130 are biased inwardly against the outer wall 111 of the member 100 as they engage the tissue segments "T1" and "T2". For instance, as shown in FIG. 3C, a barb 1302 which has engaged the tissue segment "T2" is bent radially inwardly forming an angle "θ2" with respect to the longitudinal axis "L." The angle "θ2" of the stressed condition is less than the angle "θ1" of the unstressed condition, and may approach 0°. As seen in FIG. 3A, although the barb 1302 is in contact with the tissue segment "T2", the barb 1302 does not penetrate tissue segment "T2" during insertion of the member 100 into the gap "G".

Figure 4:
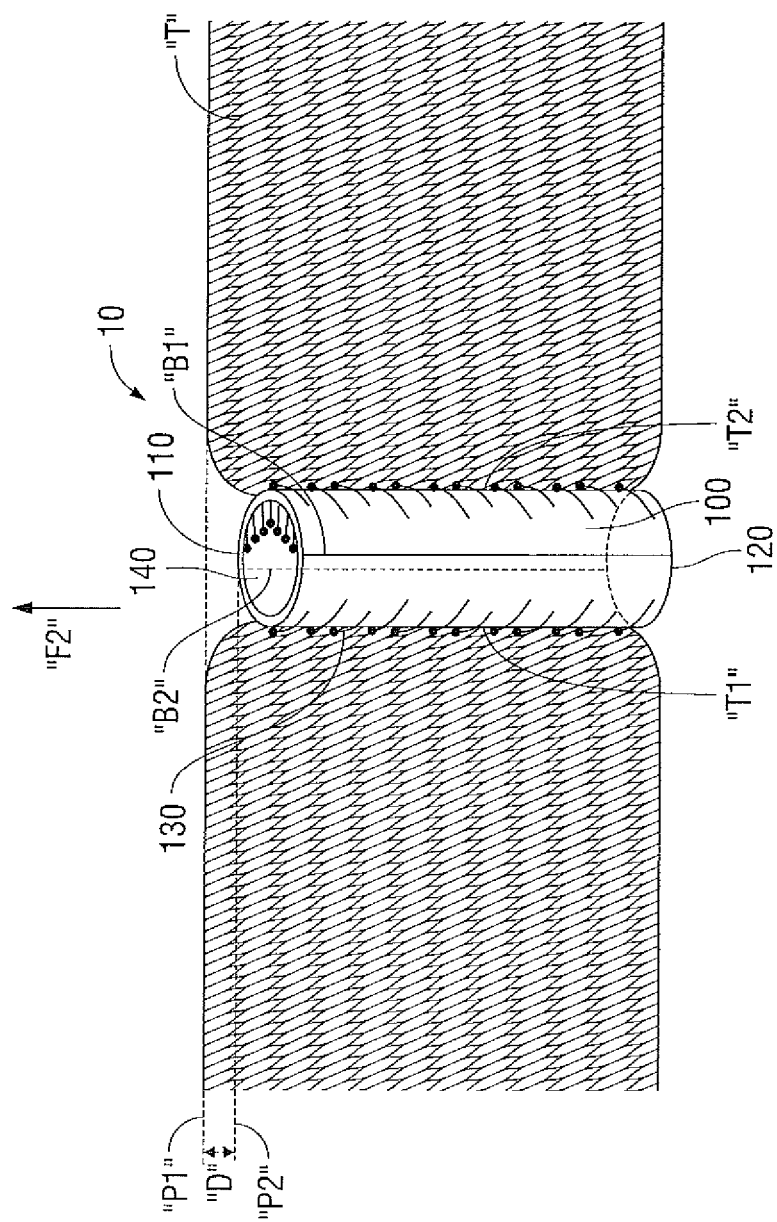
FIG. 4 is a front perspective view of the wound closure device of FIG. 1A fully deployed in the wound gap with barbs remaining in the flexed position.

The force "F1" is continuously applied to the device 10 until the member 100 is fully deployed in the gap "G" to the extent as shown in FIG. 4, where the proximal end 110 of the member 100 is distally beneath the surface "P1" of the wound opening. When the member 100 is fully deployed, the member 100 in its entirety is positioned within the gap "G", and all barbs 130 are in the flexed position in contact with the tissue segments, but have not penetrated the tissue segments.

Figure 5:
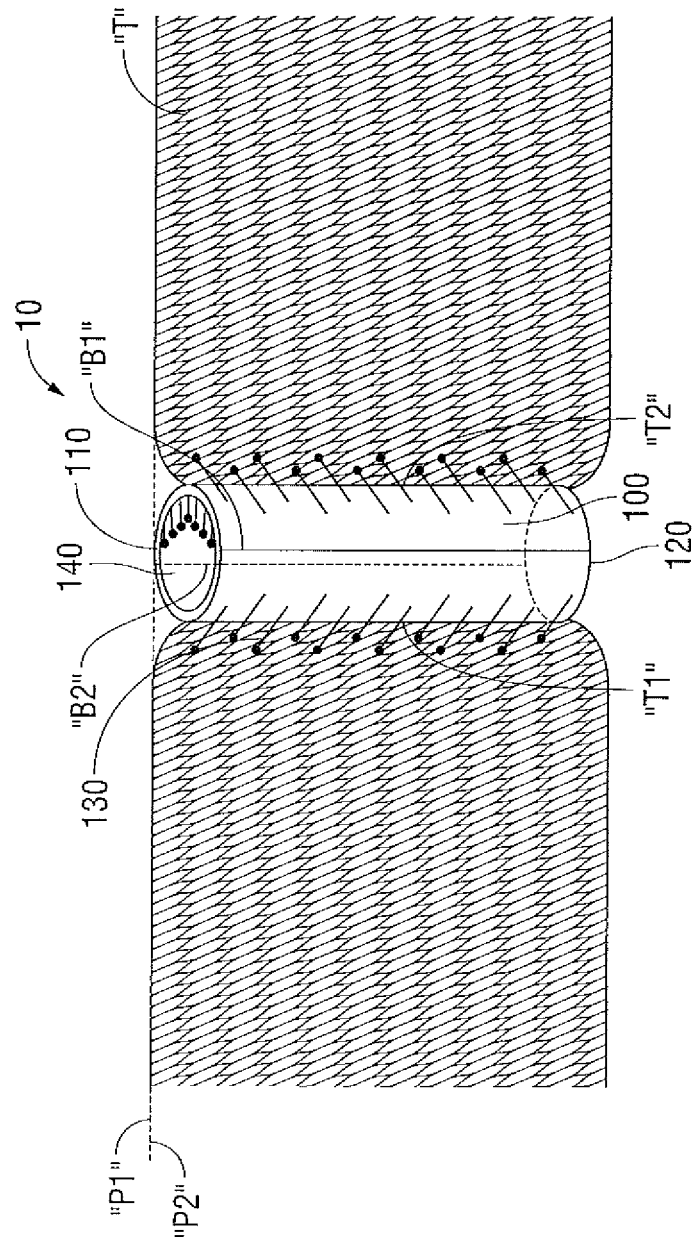
FIG. 5 is a front perspective view of the wound closure device of FIG. 1A fully deployed in the wound gap with barbs in the straightened position.

After the member 100 is fully deployed as illustrated in FIG. 4, a proximal force "F2" is applied to the device 10 to lift the device 10 in a proximal direction until the proximal end 110 of the member 100 reaches the surface "P1" of the wound opening, such that the surface "P2" of the proximal end 110 of the member 100 is coplanar with respect to the surface "P1" of the wound opening as illustrated in FIG. 5. As the member 100 moves proximally, the tissue segments "T1" and "T2" exert a force in a distal direction upon the barbs 130, causing the body 131 and the head 132 of the barbs 130 to move distally relative to the member 100, thereby returning the barbs 130 from their flexed positions to their straightened positions. As each barb 130 become fully straightened, its body 131 extends and penetrates into the tissue segment, and its head 132 grasps the tissue segment and securely attaches the tissue segments "T1" and "T2" to the member 100. Because the barbs 130 are placed along the length of the member 100, the entire length of the member 100 is thus able to engage tissue segments "T1" and "T2".

Figure 6:
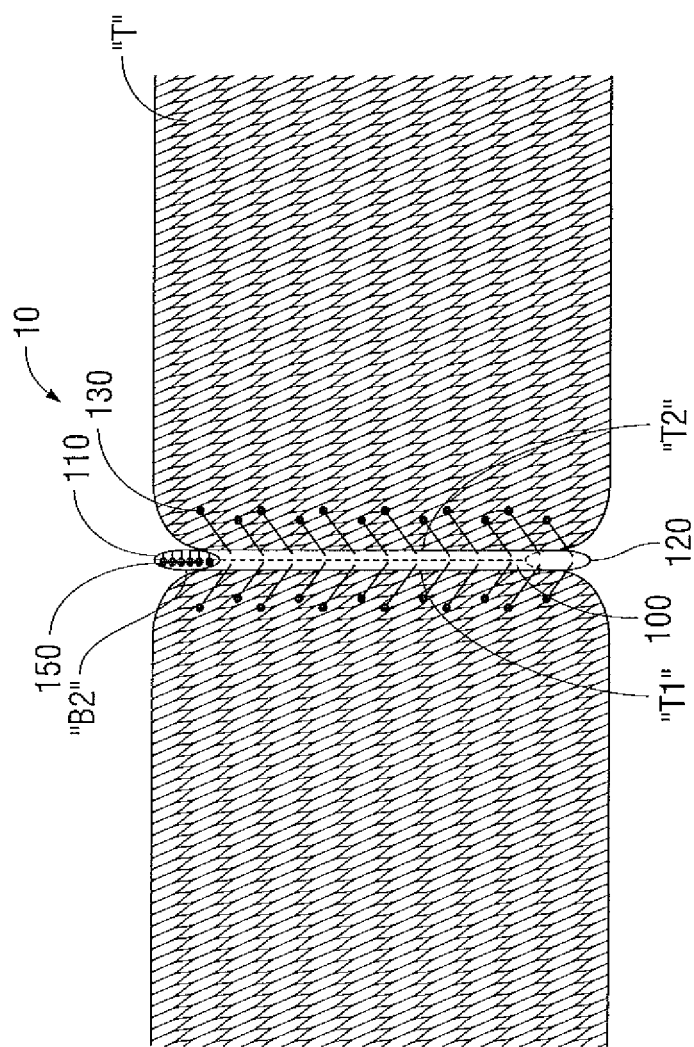
FIG. 6 is a front perspective view of the wound closure device of FIG. 1A in its second, collapsed configuration while fully deployed in the wound gap.

After the barbs 130 are engaged with the tissue segments "T1" and "T2", the member 100 is moved from its first, expanded configuration to its second, collapsed configuration as shown in FIG. 6, by the application of an external force, e.g., vacuum, or due to the inherent characteristics of the material used to construct the member 100, e.g., shape memory material. In the second, collapsed configuration, the inner wall 112 closes upon itself substantially diminishing the hollow bore 140. The barbs 150 or alternate structure located at one side of selected locations of the inner wall 112 engage the opposing side of the inner wall 112 to retain the member 100 in the collapsed configuration. This transition brings the tissue segments "T1" and "T2" to a degree of proximity that reduces and substantially closes the wound gap "G". By allowing the entire length of the member 100 to engage tissue segments, tissue segments are maintained in close approximation along the length of the wound to facilitate healing.

Please note that features described above with respect to the tubular collapsible member 100 and the tissue engaging structure 130 also apply to all embodiments of the wound closure device 10 described below.

In one embodiment, the device 10 is fabricated, at least in part, from a resilient, semi-resilient, compressible, and flexible type material that has sufficient compliance to form a seal against tissue segments. In one embodiment, the device 10 is made, at least in part, from shape memory polymeric materials which enables the device 10 to possess a permanent shape and a temporary shape. The first, expanded configuration of the device 10 represents its temporary shape, whereas the second, collapsed configuration of the device 10 represents its permanent shape. As specifically shown in FIGS. 1A-1B, in its first configuration or its temporary shape, the device 10 extends radially outwardly from a plane "B" indicated by dotted lines "B1", "B2", "B3" and "B4", whereas in its second configuration or its permanent shape, the entirety of the device 10 lies substantially within the plane "B". The device 10 reverts from its temporary shape to its permanent shape by collapsing upon itself or shrinking towards the plane "B".

Shape memory polymers are a class of polymers that, when formed into an object such as a wound closure device 10, can be temporarily deformed by mechanical force and then caused to revert back to an original shape when stimulated by energy, such as heat or light. Shape memory polymers exhibit shape memory properties by virtue of at least two phase separated microdomains in their microstructure. The first domain is composed of hard, covalently cross-linked or otherwise chain motion-limiting structures, which act as anchors to retain the object's original shape. The second domain is a switchable soft structure, which can be deformed and then fixed to obtain a secondary or temporary shape.

In the case of heat stimulated shape memory polymers, a transition temperature ($T_{Trans}$) exists at which a shape memory material changes from its primary shape to the temporary shape. A permanent temperature ($T_{perm}$) also exists at which the shape memory material reverts from the temporary shape to the permanent shape. In one embodiment, the permanent temperature ($T_{perm}$) is within the range of normal body temperatures, such that once the device 10 is fully inserted between the tissue segments, the device 10 automatically reverts back to its permanent shape, i.e., the second, collapsed configuration due to the temperature of the surrounding tissue segments. In embodiments in which a higher shape memory temperature is desired, heating can be accomplished by using a gas or liquid heating medium, heating devices, ultrasonic waves, electrical induction, chemical reaction, and the like. The means for this heating, however, is not limited. Of course, in an application involving a living body, care must be taken to utilize a heating temperature which will not cause burns. Examples of liquid heating media include, physiological saline solution, alcohol, combinations thereof, and the like.

Additionally, it is also envisioned that the shape memory material may recover its permanent shape upon contacting bodily fluids, such that the device 10 reverts to its second, collapsed configuration upon contacting bodily fluids emanated from the tissue segments after being fully deployed in the wound gap "G".

In embodiments, the shape memory material is a crosslinked polyurethane made by using excess diisocyanate or by using a crosslinker such as glycerin or trimethylol propane. Other suitable non-degradable materials include, but are not limited to, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polytetramethylene ether glycol; polybutesters, including copolymers of butylene terephthalate and polytetramethylene ether glycol; 1,4-butanediol; polyurethanes; acrylic polymers; methacrylics, vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

Figure 7A:
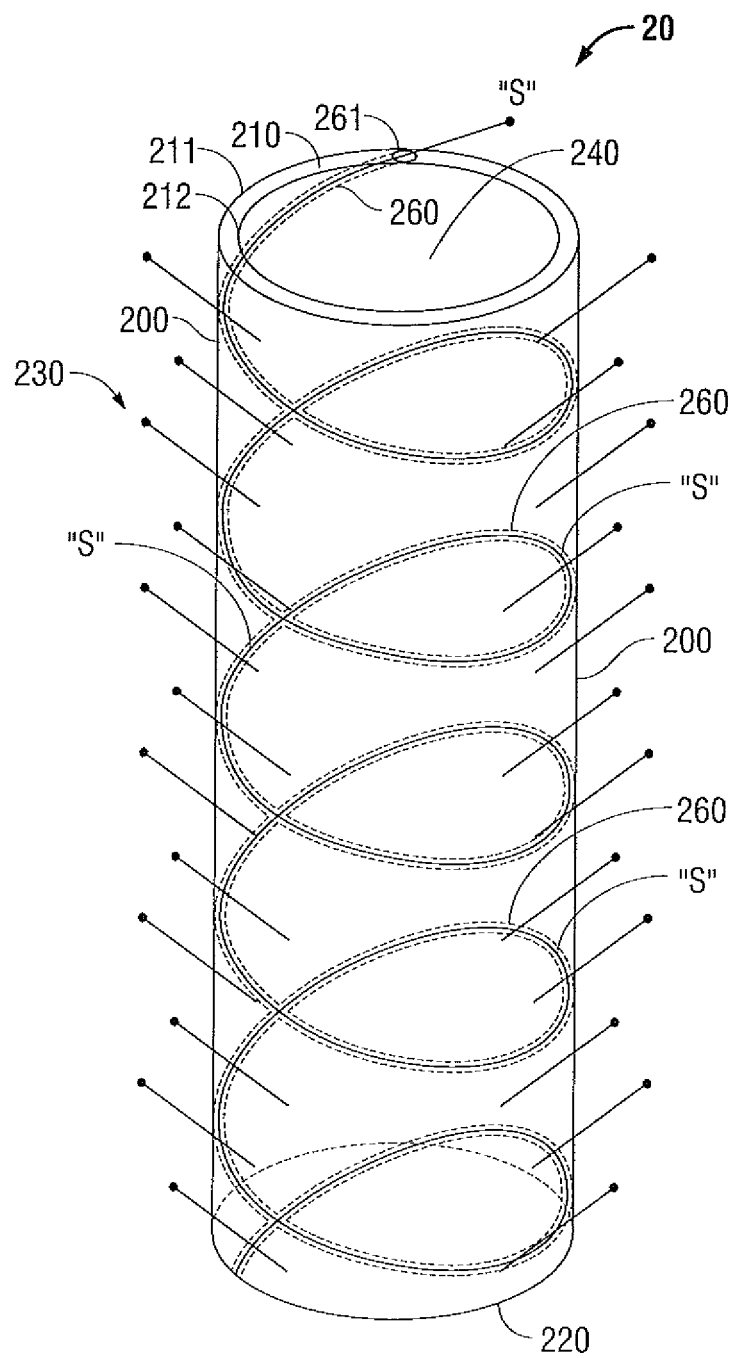
FIG. 7A is a front perspective view of an alternate embodiment of the wound closure device with a suture attached thereto.

FIG. 7A illustrates another embodiment of the wound closure device 20 in which a suture "S" is predisposed within the tubular collapsible member 200. A helical passage 260 is formed between the outer wall 211 and the inner wall 212 of the member 200. The helical passage 260 stretches from the proximal end 210 to the distal end 220 of the member 200 with an opening 261 at the proximal end 210. The suture "S" is disposed within the helical passage 260 with a distal end secured to the distal end 220 and a proximal end reaching proximally beyond the opening 261 of the passage 260. An application of force on the proximal end of the suture "S" in the proximal direction pulls out a certain amount of the suture "S" from the helical passage 260. As a result of pulling the suture "S", a lesser amount of the suture "S" is left in the passage 260 as seen in FIG. 7C. Due to this application of force, the device 200 transits from its first, expanded configuration shown in FIG. 7A to its second, collapsed configuration shown in FIG. 7C.

Figure 7B:
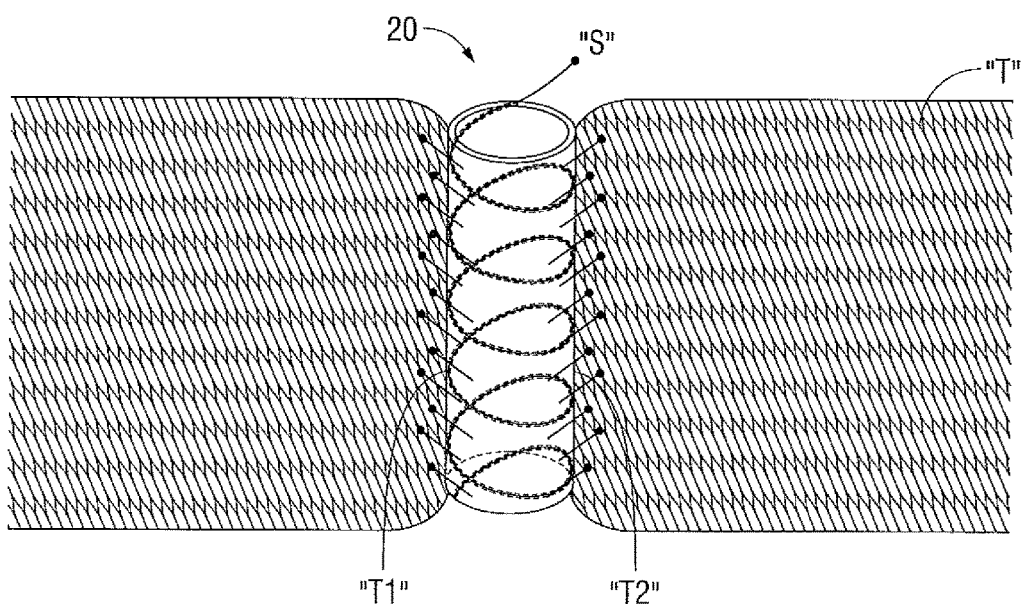
FIG. 7B is a front perspective view of the wound closure device of FIG. 7A deployed in the wound gap.
Figure 7C:
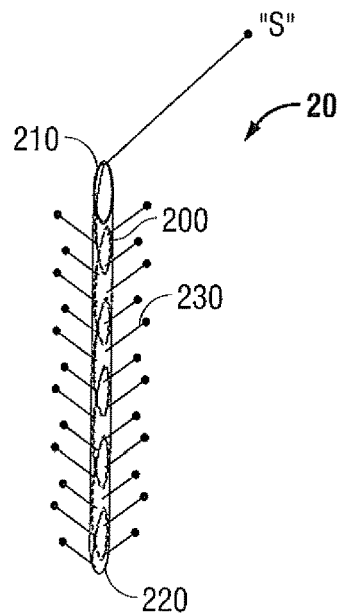
FIG. 7C is a front perspective view of the wound closure device of FIG. 7A in the second, collapsed configuration.
Figure 7D:
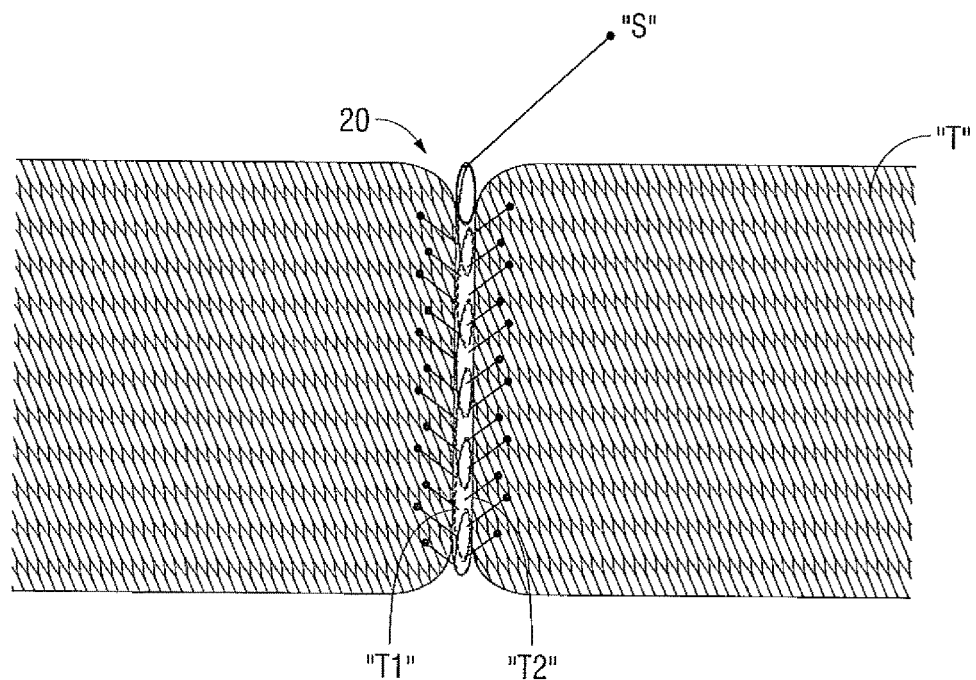
FIG. 7D a front perspective view of the wound closure device of FIG. 7C deployed in the wound gap.

With reference to FIGS. 7B and 7D, during operation, after the device 20 is fully deployed into the wound gap "G" and after the barbs 230 penetrate into the tissue segments "T1" and "T2", pulling the suture "S" in a proximal direction completes the closure of the gap "G".

Figure 8A:
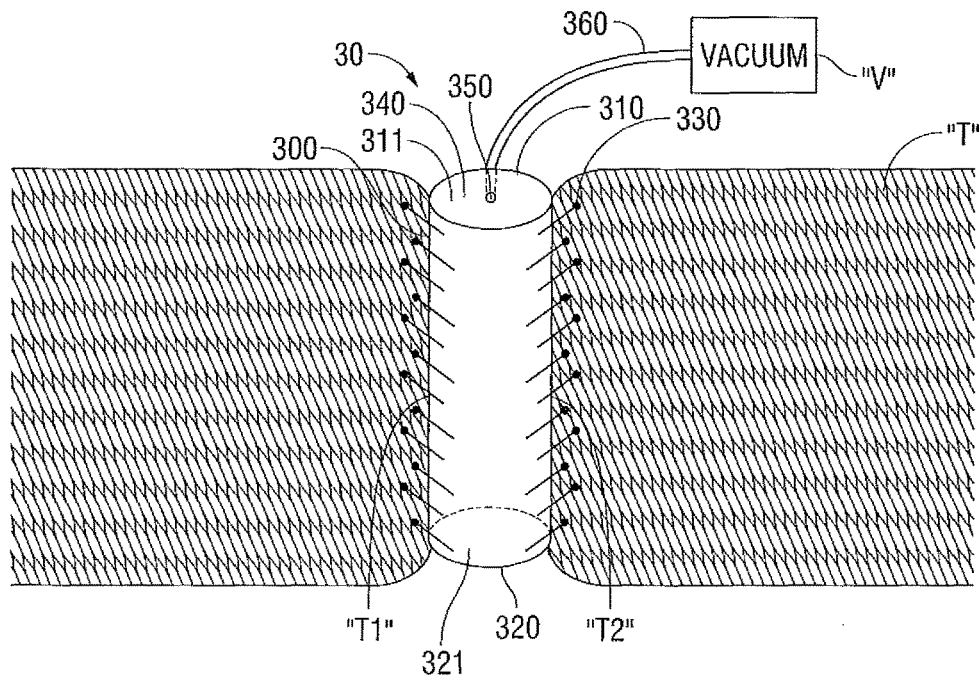
FIG. 8A is a front perspective view of another alternate embodiment of the wound closure device in the first, expanded configuration operatively connected to a vacuum.
Figure 8B:
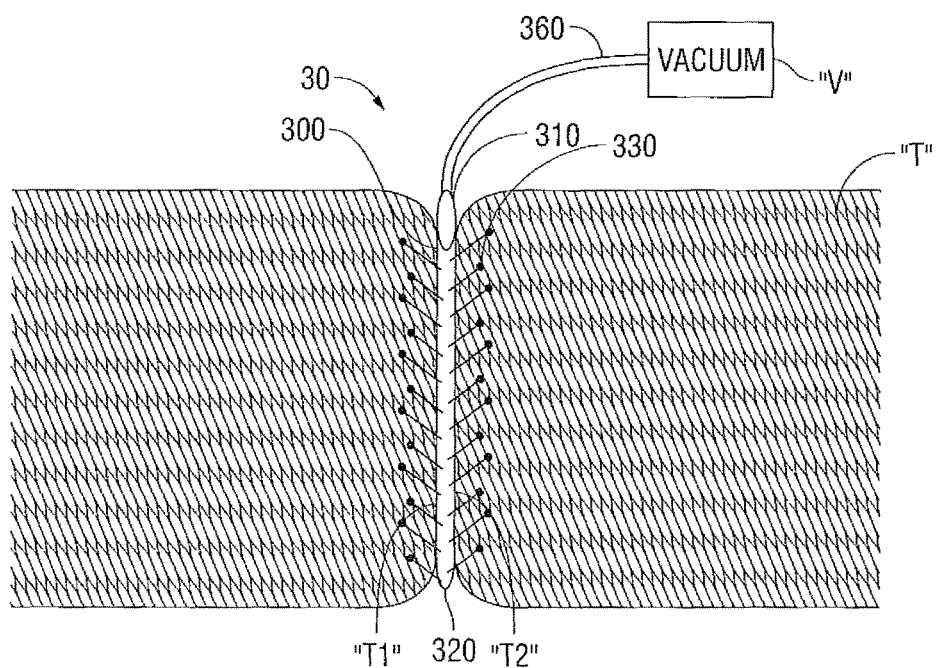
FIG. 8B is a front perspective view of the wound closure device of FIG. 8A in the second, collapsed configuration.

In another alternate embodiment of the wound closure device 30 as illustrated in FIGS. 8A-8B, the device 30 is operatively connected to a vacuum "V" which operates to evacuate air from the hollow bore 340 to achieve the result of completely diminishing the hollow bore 340 and simultaneously transiting the tubular collapsible member 300 from its first, expanded configuration shown in FIG. 8A to its second, collapsed configuration shown in FIG. 8B. In such an embodiment, the proximal end 310 and the distal end 320 of the tubular collapsible member 300 may be closed by a proximal cover 311 and a distal cover 321, respectively. As such, the covers 311, 321 together with the inner wall of the tubular collapsible member 300 define a confined space within the member 300. The covers 311 and 321 may be integrated with the member 300 or may be separate components releasably attached to the member 300. The covers 311 and 321 may comprise resilient, semi-resilient, compressible, and flexible type material, and may also comprise shape memory material as discussed earlier. The vacuum "V" applies negative pressure to the hollow bore 340 through a conduit 360. In one embodiment, the conduit 360 is connected an opening 350 defined through the inner wall and the outer wall of the member 300, such that air is withdrawn from the hollow bore 340 through the opening 350 and the conduit 360 into the vacuum "V". Alternately, other mechanisms of connecting the vacuum "V" to the member 300 are envisioned.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A wound closure device for closing a wound gap, the wound closure device comprising:
    a unitary collapsible member defining a longitudinal axis and a bore and having an outer wall with an outer surface; and
    tissue engaging structure extending radially outwardly from the outer surface of the outer wall of the collapsible member along the length of the collapsible member, the tissue engaging structure being configured to engage tissue to anchor the collapsible member to the tissue;
    wherein the collapsible member is dimensioned to be received within the wound gap such that the tissue engaging structure engages the tissue defining the wound gap, the collapsible member defining a first configuration in which the bore is open and a second configuration in which the bore is closed, the collapsible member being collapsible from the first configuration to the second configuration to close the wound gap.

2. The wound closure device according to claim 1, wherein the wound closure device is fabricated from a shape memory material.

3. The wound closure device according to claim 2, wherein the collapsible member is formed from material that transitions from the first configuration to the second configuration at a predetermined temperature.

4. The wound closure device according to claim 2, wherein the collapsible member is formed of material that transitions from the first configuration to the second configuration when contacting a predetermined fluid.

5. The wound closure device according to claim 1, wherein the tissue engaging structure comprises a plurality of barbs configured to penetrate the tissue.

6. The wound closure device according to claim 5, wherein the plurality of barbs are configured to flex upon contacting the tissue during movement of the collapsible member in an insertion direction into the wound gap.

7. The wound closure device according to claim 5, wherein the plurality of barbs define a first angle with respect to the longitudinal axis of the collapsible member before contacting the tissue.

8. The wound closure device according to claim 7, wherein the plurality of barbs define a second angle with respect to the longitudinal axis upon contacting the tissue when the collapsible member enters the wound gap and is advanced in an insertion direction.

9. The wound closure device according to claim 8, wherein the first angle is different from the second angle.

10. The wound closure device according to claim 8, wherein the plurality of barbs return to the first angle with respect to the longitudinal axis upon an application of force in a direction opposite to the insertion direction.

11. The wound closure device according to claim 1, wherein the tubular collapsible member is operatively connected to a vacuum such that the vacuum facilitates the transition of the collapsible member from the first configuration to the second configuration.

12. The wound closure device according to claim 1, further comprising a suture disposed in the collapsible member.

13. The wound closure device according to claim 12, wherein the collapsible member defines a helical passage extending from a distal end of the collapsible member to a proximal end, and the suture is accommodated within the helical passage.

14. The wound closure device according to claim 13, wherein the suture is movable within the helical passage upon an application of force on the suture to effect movement of the collapsible member from the first configuration to the second configuration.

15. The wound closure device according to claim 1, wherein the collapsible member is tubular.

16. The wound closure device according to claim 15, wherein the bore is hollow.

* * * * *